United States Patent [19]

Fulmer et al.

[11] Patent Number: 5,580,623
[45] Date of Patent: Dec. 3, 1996

[54] STORAGE STABLE PARTIALLY NEUTRALIZED ACID COMPOSITIONS AND USES

[75] Inventors: Mark Fulmer, Santa Clara; John Ross, Stanford; Brent Constantz, Scotts Valley, all of Calif.

[73] Assignee: Norian Corporation, Cupertino, Calif.

[21] Appl. No.: 469,898

[22] Filed: Jun. 6, 1995

Related U.S. Application Data

[63] Continuation of Ser. No. 96,161, Jul. 22, 1993, abandoned.

[51] Int. Cl.$^6$ .............................. A61F 2/28; C01B 15/16
[52] U.S. Cl. ..................... 428/34.1; 423/308; 423/309; 423/311; 423/317; 433/199.1; 433/201.1; 433/228.1; 433/212.1; 623/16; 206/219; 206/524.5; 106/35
[58] Field of Search ................... 428/34.1; 423/308, 423/309, 311, 317; 433/199.1, 201.1, 228.1, 212.1; 623/16; 206/219, 524.5; 106/35

[56] References Cited

U.S. PATENT DOCUMENTS

| | | | |
|---|---|---|---|
| 3,679,360 | 7/1972 | Rubin | 23/109 |
| 3,787,900 | 1/1974 | McGee | 3/1 |
| 3,913,229 | 10/1975 | Driskell | 32/15 |
| 4,097,935 | 7/1978 | Jarcho | 3/1.9 |
| 4,481,175 | 11/1984 | Iino | 423/308 |
| 4,503,147 | 3/1985 | Hatahira | 501/1 |
| 4,612,053 | 9/1986 | Brown | 706/35 |
| 4,659,617 | 4/1987 | Fuhii | 428/221 |
| 4,693,986 | 9/1987 | Vit | 501/1 |
| 4,917,702 | 4/1990 | Scheicher | 623/16 |
| 5,053,212 | 10/1991 | Constanz et al. | 423/305 |
| 5,129,905 | 7/1992 | Constanz | 606/76 |
| 5,149,368 | 9/1992 | Liu | 424/602 |
| 5,178,845 | 1/1993 | Constanz et al. | 423/305 |
| 5,336,264 | 8/1994 | Constanz et al. | 623/16 |

FOREIGN PATENT DOCUMENTS

| | | |
|---|---|---|
| 522733 | 6/1992 | European Pat. Off. . |
| 9212044 | 1/1992 | Japan . |
| 2248232 | 1/1992 | United Kingdom . |

OTHER PUBLICATIONS

Brown et al., Variations in Solution Chemistry During the Low Temperature Formation of Hydroxyapatite, J. Am. Chem. Soc. (1991) 74: 1848–1854.

Brown and Fulmer, Kinetics of Hydroxyapatite Formation at Low Temperature, J. Am. Ceram. Soc. (1991) 74: 934–940.

Shindo et al., Facial Skeletal Augmentation Using Hydroxyapatite Cement, Arch. Otolaryngol Head Neck Surg. (1993) 119:185–189.

Yu et al., Self–Setting Hydroxyapatite Cement, J. Pharm. Sci (1992) 81:529–531.

Freidman et al., Hydroxyapatite Cement., Arch. Otolaryngol Head Neck Surg (1991) 117: 385–389.

Arends and Jongebloed, Apatite Single Crystals, Recl. Trav. Pays–Bas (1981) 100: 3–9.

Chohayeb et al, Evaluation of Calcium Phosphate as a Root Canal Sealer, J. Endodontics (1987) 13:384–387.

Ohwaki et al, Summary, The 13th Annual Meeting of the Society for Biomaterials, Jun. 6, 1987, New York, New York.

*Primary Examiner*—Charles Nold
*Attorney, Agent, or Firm*—Bertram I. Rowland; Bret E. Field; Flehr, Hohbach, Test, Albritton & Herbert

[57] ABSTRACT

Methods and compositions are provided for preparing storage stable partially neutralized acid compositions. The partially neutralized acid compositions are amenable to prolonged periods of storage. Following storage, the acids can be neutralized with a calcium neutralizing source and combined with a lubricant to form a rapidly setting calcium phosphate mineral suitable for a variety of purposes, e.g. bone replacement.

12 Claims, No Drawings

STORAGE STABLE PARTIALLY NEUTRALIZED ACID COMPOSITIONS AND USES

This is a continuation of application Ser. No. 08/096,161 filed Jul. 22, 1993, now abandoned.

INTRODUCTION

1. Technical Field

The field concerns the preparation of partially neutralized acid compositions and their use in the preparation of calcium phosphate minerals.

2. Background

A number of calcium phosphate minerals, such as hydroxyapatite, fluorapatite, octacalcium phosphate (OCaP), whitlockite (Beta-TCP), brushite and monetite, do, or may, find application as biocompatible minerals. The various crystalline forms have different properties which in particular applications may be more or less desirable. For example, OCP ($k_{sp}=10^{-27}$), TCP (tricalcium phosphate, alpha or beta form or $Ca_{3-x}Mg_x(PO_4)_2$ ($k_{sp}=10^{-27}$) are resorbable, while brushite ($CaHPO_4 \cdot 2H_2O$) ($k_{sp}=10^{-7}$) and monetite ($CaHPO_4$) ($k_{sp}=10^{-7}$) are very resorbable. See Constantz et al., By forming the different minerals with their varying crystalline structures, compositions and chemical and physical properties, mineral products may be obtained having different properties for particular applications.

Apatite is a general term for a wide range of compounds represented by the general formula $M^{2+}_{10}(ZO_4^{3-})_6Y^-_2$, wherein M is a metal atom, particularly alkali or alkaline earth metal atom, and $ZO_4$ is an acid radical, where Z may be phosphorous, arsenic, vanadium, sulphur or silicon, or may be substituted in whole or in part with carbonate ($CO_3^{2-}$). Y is an anion, usually halide, hydroxy, or carbonate.

Hydroxyapatite, as well as modified forms thereof, assumes substantial interest and importance by virtue of the fact that it is a major naturally occurring building block in bone, teeth, and some invertebrate skeletons. There are many situations where bone has been broken, destroyed, degraded, become too brittle, or been subject to other deteriorating effects. In many of these situations, it would be desirable to be able to replace the bone structure or strengthen the bone structure. In providing materials to substitute for natural bone, there are a number of restraints on the nature and composition of the material.

The material should be physiologically acceptable, so as to avoid the initiation of clots, inflammatory response, and the like. Two different product forms are desirable: One being a hydroxy- or fluorapatite which is non-resorbable in vivo; the other including substantial amounts of carbonated apatite, calcium deficient apatite, OCP, TCP, brushite, and monetite, which are resorbable in vivo. In addition, the material must be strong and not friable. Furthermore, there should be strong adhesion between the material and any remaining bone. Also, desirably, the material should be capable of assuming some of the natural role of bone, such as accommodating stem cells, allowing remodeling by osteoclasis followed by new bone ingrowth, and normal metabolic calcium exchange of native bone.

Besides the biological and physiological considerations, there are the additional considerations of how the material is made and the ease with which it may be formed to a desired shape. Specifically, a material which could be injected as a liquid to fill voids and completely fill in areas deficient of hard bone is very desirable. Where the material is to be placed in situ, a variety of considerations come to the fore. For example, the rate at which the reaction occurs for formation of hydroxyapatite, as well as the change in enthalpy of the reaction, are important. Where the reaction is highly exothermic, it may not be tolerated by the patient. The form in which it is introduced must be stable in the environment in which it is introduced, so that not only must the final product be stable, but the intermediate products must also be stable as the reaction occurs.

Additionally, storage stable packaged kits for the production of apatites may be desired so that orthopedic practitioners can keep a supply of more readily available apatitic cement in inventory for immediate use. Such kits may typically contain premeasured amounts of apatite forming ingredients and, as such, require the handling, packaging, and shipping of concentrated phosphoric acid. An ideal kit would provide both storage stability, and largely dispense with the complications associated with the packaging and handling of concentrated acids.

It has therefore been found difficult to provide physiologically useful forms of hydroxyapatite and/or other calcium phosphate minerals. For the most part, the hydroxyapatites and other calcium phosphate bone grafting particulates that have been available have lacked one or more of the properties necessary for a useful implant, and, therefore, have failed to obtain general acceptance.

RELEVANT LITERATURE

Patents of interest include U.S. Pat. Nos. 3,787,900; 3,913,229; 3,679,360; 4,097,935; 4,481,175; 4,503,157; 4,612,053; 4,659,617; 4,693,986; 5,149,368; and 4,917,702. Other patents of intereste include European Patent Application No. 92305693.0; U.K. Patent Application No. 2,248, 232; Jap. Pat. App. Nos. 4012044 and 4-29907.

Fulmer et al., *J. Mat. Sci.*(1992) 3:299–305; Brown et al., *J. Am. Ceram. Soc.* (1991) 74:1855; and Fulmer et. al., *J. Am. Ceram. Soc.* (1991) 74:934–940 describe various aspects of hydroxyapatite formation.

Shind et al., *Arch. Orontaryngol. Head Neck Surg.* (1993) 119:185 describes the use of hydroxyapatite cement in facial implant. Yu et al., *J. Pharm, Sci.* (1992) 81:529 demonstrates the use of hydroxyapatite cements as drug delivery systems to skeletal tissues. Constantino et al., *Arch. Orontaryngol. Head Neck Surg.* (1991 ) 117:379 describes the histological response to implants of hydroxyapatite.

See also, Arends and Jongebloed, *Rec. Tray. Chim. Pays-Bas* (1981) 100:3–9. Use of calcium phosphate as a sealer-filler material is described in Chohayeb et al., *J. Endodontics* (1987) 13:384–387. See also, Ohwaki et al., *13th Ann. Mtg. of the Soc. for Biomaterials*, Jun. 2–6, 1987, New York, N.Y., p209.

SUMMARY OF THE INVENTION

Partially neutralized acid compositions are prepared by mixing under substantially anhydrous conditions, a highly concentrated phosphoric acid source substantially free of combined water and a neutralizing source in approximately stoichiometric amount to form a storage stable composition for subsequent formation of a calcium phosphate mineral. The partially neutralized acid compositions may remain stable after extended storage under substantially anhydrous conditions. The storage stable partially neutralized acids can subsequently be mixed with an additional neutralizing calcium source, a biocompatible lubricant, and optionally hydroxyapatite crystals, protein, or pharmacologically active agents. The components are mixed to obtain a substantially uniform dispersal and reaction of ingredients to form the desired mineral, at which time the mixture may be shaped, and allowed to remain quiescent to allow crystal formation and hardening to form a final stable form.

DESCRIPTION OF THE SPECIFIC EMBODIMENTS

Storage stable partially neutralized acid compositions may be produced by combining under substantially anhydrous conditions: an orthophosphoric acid substantially free of combined water and a neutralizing source in an amount sufficient to only partially neutralize the acid; usually at least about 20%, conveniently between about 20 percent and about 90 percent, and preferably between about 25 percent and about 75 percent of the orthophosphoric acid. (For the purposes of this invention, "neutralizing" intends that a sufficient amount of basic calcium is employed to provide the Ca:P ratio of the desired product.)The ingredients will be mixed to obtain a uniform mixture/dispersal of ingredients and may be used immediately, but will normally be stored for later use.

Both prior to and during combination, mixing, and storage, the ingredients will be maintained under substantially anhydrous conditions. Substantially anhydrous conditions may be low humidity conditions with conveniently less than about 25 percent relative humidity, and preferably less than about 20 percent relative humidity. Substantially anhydrous conditions may be maintained by any of a number of techniques known to one of ordinary skill in the art including but not limited to: heating the ingredients or final mixture to evaporate and remove water; combining, mixing, and storing the ingredients or final mixture in a low humidity environment such as a dry box; dry nitrogen gas purges; desiccation or vacuum-desiccation; or maintaining the final mixture under low humidity conditions by enclosure in a hermetically sealed package in order to sequester the product from extraneous moisture. Partially neutralized acids stored as described above remain storage stable for at least about 24 hours, conveniently at least ten days, generally at least 16 days, and preferably between ten days and several months.

The source of orthophosphoric acid will generally be comprised of a crystalline form of orthophosphoric acid that is substantially free of combined water. The acid source will conveniently comprise between about 50 and 90 mole percent, and preferably between about 60 and 80 mole percent of the dry partially neutralized acid product.

The neutralizing source will be comprised of at least one of calcium carbonate, calcium hydroxide, or other basic calcium phosphates, in particular, partially neutralized calcium phosphates. Partially neutralized calcium phosphates may include tetracalcium phosphate ($Ca_4P$), tricalcium phosphate ($Ca_3P$), monocalcium phosphate ($CaP$), or metastable forms thereof. Where calcium hydroxide is used as a component of the neutralizing source, it will generally be present between about 0.1 and 20 weight percent of the ingredients of the mixture. Where calcium carbonate is used as a component of the neutralizing source it will be present between about 1 and 100 weight percent of the ingredients of the neutralizing source. Partially neutralized calcium phosphates may comprise between about 1 and 100 mole percent of the neutralizing source. Preferably, a combination of a calcium phosphate and calcium carbonate will be used, where the carbonate is not more than about 80 weight percent.

In general, the neutralizing source will be added in an amount sufficient to provide a partially neutralized acid with final Ca:P ratio of between 0.2 and 0.7, and preferably about 0.5.

The partial neutralization reaction may occur over a wide range of temperatures. Conveniently, the reaction temperature will be greater than about minus 80° C., or in the range between about minus 80° C. and 65° C., more generally between about 4° C. and 42° C., and preferably, about room temperature.

Mixing of the combined orthophosphoric acid and neutralizing source may be in any manner that will provide a uniform mixture or dispersal of ingredients, and a partial neutralization of the acid source. Varying types of equipment can be used for these purposes, including but not limited to: ball milling, Brabender mixing, mortar and pestle, planetary mills, vibratory mills, and the like. Of particular interest is mixing by milling to place the acid source and neutralizing source in intimate contact. Mixing/milling to provide a uniform mixture will generally proceed for about 15 seconds to about 30 minutes.

Partially neutralized acid products produced as described above will find utility in the preparation of apatitic calcium phosphate products, carbonated apatites, or otherwise substituted forms of apatite. In general, storage stable partially neutralized acids will be mixed with a neutralizing calcium source and a biocompatible lubricant, and allowed to remain quiescent while hardening into a apatitic structure with a substantially complete reaction of the partially neutralized acid source and neutralizing calcium source. Optionally, pharmacologically active agents, structural proteins, or crystalline nuclei, particularly hydroxyapatite, may be added not later than the substantially complete reaction.

The partially neutralized acid source will generally comprise between about 25 and 80 percent of the dry ingredients by weight.

The neutralizing calcium source may be comprised of any of the ingredients used in the neutralizing source listed above, and alternatively, it may be identical to the neutralizing source. Where a dahllite product is desired, the neutralizing calcium source will contain $CaCO_3$ in an amount sufficient to provide a final apatitic product comprising between about 2 mole percent and about 8 mole percent carbonate. The neutralizing calcium source will be added in an amount sufficient to substantially completely neutralize the partially neutralized acid source, and provide a final calcium to phosphate ratio in the range between about 1.0 and 2.0, preferably about 1.67. Conveniently, the neutralizing calcium source will comprise between about 20 and 75 percent of the dry weight of the mixture.

The biocompatible lubricants may include, but not be limited to, any from a group of physiologically compatible solvents such as: water or purified forms thereof, aqueous alkanols, e.g. glycerol, where the alkanol is present in minor amounts, preferably less then about 20 percent, pH buffered or non-buffered solutions, and the like.

By varying the amount of lubricant added to the final mixture, the fluidity of the composition can be varied with respect to flowability and viscosity. Thus, implantation may be by syringe or catheter injection. Where an injectable composition is desired, the composition may flow through a needle of between about 10 and 18 gauge, or preferably between about 14 and 16 gauge. Alternatively, lubricant may be added in an amount sufficient to provide a kneadable or moldable product.

Mixing of the partially neutralized acid source, neutralizing calcium source, and lubricant may be by any of a variety of the above-mentioned mechanical or manual means, and will proceed to provide a substantially uniform dispersal of ingredients. Conveniently, mixing will occur for about 15 seconds to several minutes. After mixing, a product is produced that is capable of forming a solid apatite with substantially complete reaction of the partially neutralized acid source and calcium source. The mixture may be formed and allowed to harden, or injected directly in situ and allowed to harden. During hardening, a substantially complete reaction of the acid and neutralizing sources occurs, crystal growth occurs, and the mixture anneals into a monolithic product. Substantial hardening will take at least about 10 minutes, and preferably not more then about 2 hours.

A substantially complete reaction may be defined as when at least about 75 percent, generally at least about 90 percent, and preferably at least about 95 percent of the available acid groups are neutralized.

Various additional components may be included during the formation of the final apatitic product. Of particular interest are pharmacologically active agents, proteins, or the like. Pharmacologically active agents might include drugs that enhance bone growth, serve as a variety of cell growth factors, or act as anti-inflammatory or anti-microbial agents. Of particular interest are proteins involved in skeletal structure such as different forms of collagen, especially Type I, fibrin, fibrinogen, keratin, tubulin, elastin, and the like. Other useful proteins might include: bone morphogenetic protein, cartilage induction factor, platelet derived growth factor, and skeletal growth factor.

Pharmacologically active agents may be added to about 0.2 to about 2 parts per 100 parts by weight as an aqueous dispersion or solution. Usually protein may be present at from about 1 to about 10 weight percent of the aqueous dispersion. The amount of water added to the compositions to which protein in aqueous dispersion has also been added will be adjusted accordingly.

By varying the proportions of the reactants, compositions with varying and predictable rates of resorption in vivo, can be made. Thus, the subject compositions may serve as implantable or injectable time-release delivery platforms for drugs, mineral supplements, or the like. Where the above embodiments are desired, the subject compositions may be combined with pharmacologically active agents and/or inorganic components prior to, or during mixing, and generally not later then the complete reaction of the partially neutralized acid source and neutralizing calcium source. The amount of additive will generally vary between about 0.1 to about 25 weight percent of the inorganic materials. It may be preferred that the additive be combined with the inorganic materials before mixing.

Another embodiment of the present invention is the production of apatitic products from a storage stable kit comprising premeasured amounts of the ingredients: a partially neutralized acid source, a neutralizing calcium source, a biocompatible lubricant, and, optionally, a pharmacologically active or protein additive, in which each ingredient is separately stored in hermetically sealed containers. Prior to use, the seals on the various containers may be broken, and the ingredients combined and mixed. Unlike previous kits for the formation of apatitic products, the subject kits avoid the complications and hazards associated with packaging and shipping premeasured amounts of orthophosphoric acid. Moreover, since the partially neutralized acid source was produced under substantially anhydrous conditions and is packaged in a hermetically sealed case, the relative absence of water, as compared to previously disclosed partially neutralized acid compositions, results in a partially neutralized acid composition with substantially enhanced storage life.

The following examples are offered by way of illustration and not by way of limitation.

EXPERIMENTAL

Example 1

Partially neutralized orthophosphoric acid (oPA) compositions were produced as summarized below:

| 1. Mixture #1 | | 2. Mixture #2 | |
|---|---|---|---|
| oPA | 2.058 g | oPA | 2.685 g |
| $C_4P$ | 1.128 g | $CA(OH)_2$ | 1.015 g |
| $CaCO_3$ | 0.070 g | | |
| 3. Mixture #2 | | 4. Mixture #4 | |
| oPA | 2.685 g | oPA | 2.013 g |
| $CaCO_3$ | 1.371 g | $C_4P$ | 1.254 g |
| 5. Mixture #5 | | | |
| (Control-No Neutralization of Acid Source) | | | |
| oPA | 2.058 g | | |
| $C_4P$ | 11.54 g | | |
| $CaCO_3$ | 1.402 g | | |

The acid source and neutralizing sources were combined to produce a 0.5:1 Ca/P ratio. Each of the combined powders were mixed in a substantially anhydrous atmosphere (20 percent relative humidity±5 percent) for thirty seconds using a mortar and pestle where partial reaction occurred. Room temperature was maintained at 20°–22° C. throughout the process. A portion of the partially neutralized acids produced by the above protocol were subject to Fourier transform infrared spectroscopy (FTIR) or X-ray diffraction (XRD) analysis demonstrating that partial neutralization of from 75 to 100 percent of the potential neutralization had occurred.

After partial neutralization, a neutralizing calcium source (10.41 g $C_4P$ and 1.3315 g $CaCO_3$) was added and the ingredients were lightly mixed for fifteen seconds to obtain a substantially uniform dispersal of ingredients. A biocompatible lubricant (0.075M $Na_2HPO_4$) was added to the dry ingredients at a liquid to solid weight ratio of 0.56 and mixed for 3 minutes to obtain a substantially uniform dispersal of ingredients. The mixture was subsequently allowed to remain quiescent to facilitate hardening.

After twenty four hours of hardening, FTIR and XRD analysis of the final products showed that all of the partially neutralized acids were capable of participating in apatite forming reactions. Mixture #3 produced apatitic products with compressive strength significantly higher then control apatites made by the conventional mixing of an orthophosphoric acid source and a calcium source. The calcium carbonate neutralized acid resulted in products that were slower in hardening than the control sample.

Mixture #1 produced a product with overall mechanical attributes similar to the control products. Moreover, FTIR and XRD analysis of the partially neutralized acid in Mixture #1 identified a combination of monocalcium phosphate monobasic (MCPM) and monocalcium phosphate anhydrous (MCPA). This combination was labeled MCPX, stored, and ultimately mixed with the neutralizing source to give the calcium phosphate mineral.

Example 2

To test the storage stability of partially neutralized acids, samples of calcium carbonate neutralized acid and MCPX were prepared as described in mixtures #1 and #3, and sealed in foil under a dry nitrogen gas atmosphere. After ten days of storage, the samples were each combined with a neutralizing calcium source and lubricant, and tested for apatite formation. The control for this experiment was mixture #5, as described in Example 1. The resulting products were tested for indentation load at 17 minutes after mixing, and for compressive strength at 24 hours after mixing. The results are outlined in Table 1 below.

TABLE 1

| Formulation | Average Indentation Strength (lbs) | Average Compressive Strength (MPa) |
| --- | --- | --- |
| Mixture #1 (MCPX) | 95.3 | 31.3 |
| Mixture #2 (Ca(OH)$_2$) | 49.63 | 33.5 |
| Mixture #3 (CaCO$_3$) | 2.3 | 30.0 |
| Mixture #4 (Ca$_4$P) | Not Tested | Not Tested |
| Mixture #5 "positive" control | 94.61 | 28.65 |

The data in Table 1 indicate that MCPX (mixture #1) remained stable during the 10 day storage period in that cements made with MCPX exhibited strengths equal to or greater than the positive control (mixture #5) cements. The CaCO$_3$ partially neutralized acid (mixture #3) and Ca(OH)$_2$ partially neutralized acid (mixture #2) reacted in a manner similar to the MCPM control, but exhibited significantly lower indentation strength.

After 10 days of storage, MCPX (mixture #1) remained functionally equivalent to the freshly prepared mixture of the ingredients of MCPX in that both were capable of supporting apatite development similar to control preparations.

Example 3

To test the long term storage capacity of the partially neutralized acid MCPX (Mixture #1), MCPX was prepared as in Example 1 and sealed in a foil pouch. At increasing time periods various pouches were opened, MCPX completely neutralized with the calcium neutralizing source, and strength data obtained. The results obtained are provided below in Table 2.

TABLE 2

| Storage Time of MCPX (days) | Indentation Strength (lbs) at 20 min. | Compressive Strength (MPa) after 24 hr. period |
| --- | --- | --- |
| 0 | 100.4 ± 1 | 28.49 ± 2.9 |
| 30 | 98.1 ± 5.6 | 28.68 ± 3.4 |
| 36 | 77.7 ± 30 | Not Tested |
| 35 (Mixture combined with new mortar and pestle) | 101.1 ± 1.0 | Not Tested |
| 45 | 100.9 ± 0.2 | Not Tested |
| 93 | 100.9 ± 0.4 | 26.45 ± 2.5 |

As demonstrated in Table 2, the partially neutralized acid source stored successfully for periods in excess of 90 days. This storage capacity was determined by the strength of the product 20 minutes after mixing with the neutralizing calcium source and lubricant. The strength attained by the cements was comparable among the three partially neutralized acid sources stored for different periods of time, i.e. 0, 30, and 90 days. Thus, it appeared that storing did not have a negative effect on the attainable strength of the final cement products.

Disparities in the data, i.e. data obtained at 36 days after storage, were attributed to impurities introduced to the mixtures before storage. These impurities were believed to be present because a new mortar and pestle was not used to combine each mixture. It was found that when a new mortar and pestle were used (see data for 35 days) these disparate results did not occur.

Example 4

To compare the qualities of the MCPX composition as produced in Example 1 with MCPX mixtures formed by combining commercially available MCPM and MCPA, the following mixtures were made and results obtained.

| 1. Mixture #1 MCPM as prepared in Example #1 | | 2. Mixture #2 MCPM (commercial) | 3.453 g |
| --- | --- | --- | --- |
| 3. Mixture #3 MCPA (commercial) | 3.208 g | 4. Mixture #4 MCPM (commercial) MCPA (commercial) | 0.759 g 2.479 g |

TABLE 3

| Formulation | Indentation Strength (lbs) 16–18 min. after mixing | Compressive Strength (MPa) |
| --- | --- | --- |
| Mixture #1 | 95.3 | 31.3 |
| Mixture #2 | 0.91 | 29.02 |
| Mixture #3 | 0.21 | No Hardening |
| Mixture #4 | 0.22 | No Hardening |

Although FTIR and XRD analysis of the partially neutralized MCPX product indicates an amorphous mixture of MCPM and MCPA, neither MCPM (mixture #2) nor MCPA (mixture #3), nor both used in conjunction (mixture #4), produced cements comparable to the MCPX partially neutralized acid source as formed in Example 1. These results indicate that the process of partial neutralization is important in forming the precursor MCPX and cannot be duplicated by buying commercially available MCPM and MCPA and mixing the two in appropriate ratios.

Example 5

The fact that completely neutralized acid can not be stored successfully was demonstrated as follows. The acid source was completely neutralized with the calcium neutralizing source and the mixture was sealed for storage. The following results were obtained.

TABLE 4

| Time of Storage (days) | Indentation Strength (lbs) at 20 min. | Compressive Strength (MPa) |
| --- | --- | --- |
| 0 | 49.3 ± 41 | 28.99 ± 2.3 |
| 30 | 31.8 ± 15.2 | 28.2 ± 2.0 |

The stored mixtures did not reach the same indentation strength values attained by the partially neutralized acid mixtures. Thus, the fully neutralized acid, as compared to partially neutralized acid, would appear to be unstable for prolonged storage periods. Further, the appearance of monetite in the mixture stored for thirty days suggested that storage of the acid source and the neutralizing source together for prolonged periods is not possible.

The compositions of the subject invention provide for a simplified method for the preparation of apatite forming bioceramic cements. Unlike previous methods of preparation, the subject invention provides for storage stable partially neutralized acid compositions that may function in apatite forming reactions in which no orthophosphoric acid is separately added. Thus, kits containing premeasured amounts of storage stable partially neutralized acids, and other products required for apatite formation, do not require separately measured and sequestered portions of orthophosphoric acid.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims,

What is claimed is:

1. A storage stable partially neutralized acid composition prepared according to the method comprising:

mixing under substantially anhydrous conditions: (a) an orthophosphoric acid substantially free of combined water; and (b) a neutralizing source comprised of at least one of calcium carbonate, calcium hydroxide or a calcium phosphate in an amount sufficient to neutralize from about 25 to 75% of said orthophosphoric acid to obtain a substantially uniform mixture, whereby substantially all of said neutralizing source is reacted to produce said storage stable partially neutralized acid composition, wherein said storage stable partially neutralized acid composition has a Ca:P ratio of between 0.2 and 0.7.

2. The composition according to claim 1, wherein said mixing is by milling.

3. The composition according to claim 1, wherein said amount of said neutralizing source is sufficient to neutralize from about 25 to 75% of said orthophosphoric acid source.

4. A storage stable partialiy neutralized acid composition prepared according to the method comprising:

mixing by milling under substantially anhydrous conditions: (a) an orthophosphoric acid substantially free of combined water; and (b) a neutralizing source comprised of at least one of calcium carbonate, calcium hydroxide or a calcium phosphate in an amount sufficient to neutralize from about 25 to 75% of said orthophosphoric acid to obtain a substantially uniform mixture, whereby substantially all of said neutralizing source is reacted to produce said storage stable partially neutralized acid composition, wherein said storage stable partially neutralized acid composition has a Ca:P ratio of between 0.2 and 0.7.

5. A method of preparing a storage stable partially neutralized acid composition comprising the steps of:

mixing under substantially anhydrous conditions: (1) orthophosphoric acid substantially free of combined water, and (2) an amount of a neutralizing source comprising at least one of calcium carbonate, calcium hydroxide, and a calcium phosphate, sufficient to neutralize from about 25 to 75% of said orthophosphoric acid to obtain a substantially uniform mixture;

whereby substantially all of said neutralizing source is reacted to form a storage stable partially neutralized acid composition, wherein said storage stable partially neutralized acid composition has a Ca:P ratio of between 0.2 and 0.7.

6. A method according to claim 5, wherein said substantially anhydrous conditions are low humidity conditions.

7. A method according to claim 6, wherein said low humidity conditions are maintained by enclosure of said substantially uniform mixture in a hermetically sealed package.

8. A method according to claim 5, wherein said mixing is by milling.

9. A method according to claim 5, wherein said amount of said neutralizing source ranges from about 25 to 75% of said orthophosphoric acid.

10. A kit for the production of apatitic products comprising premeasured amounts of a storage stable, partially neutralized acid source prepared according to the method of claim 5, a neutralizing calcium source, and a biocompatible lubricant;

wherein said partially neutralized acid source is separately contained in a hermetically sealed container.

11. A method of producing an apatitic product, said method comprising:

mixing to provide a substantially uniform dispersion: (1) a storage stable partially neutralized acid source according to claim 1, (2) a neutralizing source comprising at least one of calcium carbonate, calcium hydroxide and calcium phosphate, and (3) a sufficient amount of a biocompatible lubricant to provide a flowable or kneadable mixture; and allowing said mixture to stand, whereby said apatitic product is produced.

12. A method for preparing dahllite comprising:

mixing: (1) a storage stable partially neutralized acid source according to claim 1, (2) an acid neutralizing calcium source comprising calcium carbonate and a calcium phosphate in an amount sufficient to provide dahllite comprising from about 3 to 8% carbonate by weight; and (3) a biocompatible lubricant in an amount to provide a flowable or kneadable mixture; and allowing said mixture to stand, whereby said dahllite is produced.

* * * * *